United States Patent
Kurth et al.

(10) Patent No.: US 10,365,244 B2
(45) Date of Patent: Jul. 30, 2019

(54) ION-SENSITIVE STRUCTURE AND METHOD FOR PRODUCING THE SAME

(71) Applicant: Fraunhofer-Gesellschaft zur Foerderung der angewandten Forschung e.V., Munich (DE)

(72) Inventors: Eberhard Kurth, Moritzburg (DE); Christian Kunath, Dresden (DE); Harald Schenk, Dresden (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 0 days.

(21) Appl. No.: 15/074,702

(22) Filed: Mar. 18, 2016

(65) Prior Publication Data

US 2016/0274057 A1 Sep. 22, 2016

(30) Foreign Application Priority Data

Mar. 18, 2015 (DE) .................. 10 2015 204 921

(51) Int. Cl.
  *G01N 27/414* (2006.01)
  *G01N 27/12* (2006.01)
  *G01N 27/333* (2006.01)

(52) U.S. Cl.
  CPC ....... *G01N 27/4148* (2013.01); *G01N 27/129* (2013.01); *G01N 27/333* (2013.01); *G01N 27/414* (2013.01)

(58) Field of Classification Search
  CPC .................. G01N 27/4148; G01N 27/129
  See application file for complete search history.

(56) References Cited

U.S. PATENT DOCUMENTS

| 5,288,563 A | 2/1994 | Saito et al. |
| 7,321,143 B2 | 1/2008 | Kunath et al. |
| 8,461,587 B2 | 6/2013 | Kurth et al. |
| 2005/0156584 A1* | 7/2005 | Feng .................... G01N 27/414 324/71.5 |
| 2006/0024975 A1 | 2/2006 | Ahn et al. |

(Continued)

FOREIGN PATENT DOCUMENTS

| DE | 4423289 C1 | 11/1995 |
| DE | 69805500 T2 | 1/2003 |

(Continued)

OTHER PUBLICATIONS

Bergveld, "Development of an Ion-Sensitive Solid-State Device for Neurophysiological Measurement", IEEE Trans. Biomed. Eng. BME-17, 1970, p. 70.

(Continued)

*Primary Examiner* — Wael M Fahmy
*Assistant Examiner* — Sarah K Salerno
(74) *Attorney, Agent, or Firm* — Perkins Coie LLP; Michael A. Glenn

(57) ABSTRACT

An ion-sensitive structure includes a semiconductor structure and a layer stack disposed on the semiconductor structure having a doped intermediate layer including a doping material and a first metal oxide material. The semiconductor structure is configured to change an electric characteristic based on a contact of the ion-sensitive structure with an electrolyte including ions.

23 Claims, 9 Drawing Sheets

(56) References Cited

U.S. PATENT DOCUMENTS

| | | | |
|---|---|---|---|
| 2009/0014757 A1* | 1/2009 | Takulapalli | G01N 27/4145 |
| | | | 257/253 |
| 2011/0249314 A1* | 10/2011 | Wang | G02F 1/1523 |
| | | | 359/265 |
| 2012/0018722 A1 | 1/2012 | Kurth et al. | |
| 2012/0139011 A1 | 6/2012 | Zeun et al. | |
| 2015/0060953 A1 | 3/2015 | Kunath et al. | |
| 2016/0149249 A1* | 5/2016 | Pozvonkov | C25B 9/08 |
| | | | 429/490 |

FOREIGN PATENT DOCUMENTS

| | | |
|---|---|---|
| DE | 102013109353 A1 | 3/2015 |
| WO | 9724609 A1 | 7/1997 |
| WO | 2005073706 A1 | 8/2005 |

OTHER PUBLICATIONS

Bobrov, P.V. et al., "Chemical Sensitivity of an ISFET with Ta2Os Membrane in Strong Acid and Alkaline Solutions", Leningrad State University USSR, Sensorsand Actuators B3, 1991, pp. 75-81.

Chou, Jung-Chuan et al., "Study of Ti02 Thin Films for Ion Sensitive Field Effect Transistor Application with RF SPuttering Deposition", National Yunlin University of Science and Technology, Taiwan, Japanese Journal of Applied Physics 43, 1, 2004, pp. 61-65.

Chou, Jung-Chuan et al., "Sensitivity and Hysteresis Effect in AB03 Gate pH-ISFET", National Yunlin University Taiwan, Materials Chemistry and Physics 71, 2001, pp. 120-124.

Gimmel, P. et al., "Sensors and Actuators", 4, 1991, pp. 1, 135.

Grueger, H. et al., "High Quality r.f. Sputtered Metal Oxides (Ta205Hf02)", Thin Film Solids, 2004, pp. 509-515.

Hafeman, Dean G. et al., "Light-Addressable Potentiometric Sensor for Biochemical Systems", www.sciencemag.org, Molecular Devices Corporation, Science, vol. 240, May 27, 1988, pp. 1181-1185.

Kolkovsky, VL. et al., "Reactively Sputtered Hafnium Oxide on Silicon Dioxide: Structural and Electrical Properties", Solid-State Electronics, vol. 106, www.elsevier.com/locate/sse,, 2015, pp. 63-67.

Lai, Chao-Sung et al., "pH Sensitivity improvement on 8nm Thick Hafnium Oxide by Post Deposition Annealing", Chang Gung University Tao-Yuan Taiwan, Electrochemical and Solid-State Letters 9 (3) G90-2, 2006.

Mikolajick, T. et al., "The pH-Sensing Properties of Tantalum Pentoxide Films Fabricated by Metal Organic Low Pressure Chemical Vapor Depsition", Fraunhofer Institute INtegrated Circuits Erlangen Germany, Sensors and Actuators B44, 1997, pp. 262-267.

Remy, H., "Lehrbuch der anorganischen Chemie", Band 11, 12. Auflage, Leipzig, Akad. Verlagsges. Geest and Portig, 1973, p. 148.

Roop, R.C., "Encyclopedia of the Alkaline Earth Compounds", Elsevier, 2013, p. 772.

Van Der Wal, P. Der et al., "High-k Dielectrics for Use as ISFET Gate Oxides", Proceedings of IEEE Sensors, 1997, pp. 677-680.

Voigt, H. et al., "Sensors and Actuators", 44, 1997, pp. 1-3, 441.

Yang, Chia-Ming et al., "HfOxFy Based ISFETs with Reactive Fluorine Doping for K+ Ion Detection", International Journal of Electrochemical Science, www.electrochemsci.org, vol. 9, 2014, pp. 7069-7082.

Yoshida, Shoji et al., "Development of a Wide Range pH Sensor Based on Elektrolyt-Insulator-Semiconductor Structure with Corrosion-Resistant AbOrTa20s and AbOrZr02 Double-oxide Thin Films", Tohoku University Sendai Japan, J. Electrochem. Soc. 151 (3), 2004, pp. H53-H58.

* cited by examiner

ION-SENSITIVE STRUCTURE AND METHOD FOR PRODUCING THE SAME

CROSS-REFERENCE TO RELATED APPLICATIONS

This application claims priority from German Patent Application No. 102015204921.3, which was filed on Mar. 18, 2015, and is incorporated herein in its entirety by reference.

BACKGROUND OF THE INVENTION

The present invention relates generally to an ion-sensitive structure and to a method for producing the same. The ion-sensitive structures can be used, for example, in ion-sensitive field effect transistors (ISFETs), ion-sensitive, capacitively readable EIS sensors or LAPS sensors. In particular, the present invention relates to a chemically stable multilayered structure having doped zones.

In microsystem technology of semiconductor technology, chemically stable surfaces are necessitated as chemical protection for sensor or actuator surfaces for sensors and actuators in the different fields of application, for example environmental technology, process monitoring, food technology as well as biochemistry or medical technology. When the advantages of a chemical protective layer can also be used as sensors for chemicals, this is a particular advantage for sensor technology, for a low long-term drift of the sensor in connection with a reasonable price. In particular, the above stated electrolyte-insulator-semiconductor structures can be stated as fields of applications, which can also be configured specifically as ion-sensitive field effect transistors or ion-sensitive sensors with EIS or light-addressable ion-sensitive sensors with EIS (LAPS).

Silicon is mostly used as a semiconductor of the EIS structure. All other semiconductor/insulator combinations are mostly electrically not as stable or the necessitated electrical long term stability and accuracy can only be obtained with increased effort. Further, in the field of pH measuring arrangement, glass electrodes are known. However, the disadvantages of glass electrodes with respect to semiconductor sensors are sufficiently known, as well as how the EIS structure is used for analysis. Meanwhile, semiconductor solid body electrodes are used for PH measurement in industrial measurement technology, not only for reasons of risk of glass breakage.

The EIS sensor without FET structure has the advantage that no topology edges representing a risk for chemically aggressive media interfere with the surfaces as it is still the case in the ion-sensitive field effect transistor. However, such a structure can only be read out via capacitance measurement necessitating a measurement cell with a Faraday cage. Due to recurring topology edges, a closed chemically stabile protective layer is even more important.

For producing hydrogen ion-sensitive layers, different materials have been described, such as $Ta_2O_5$ [2,3], $AL_2O_3$ [4], $TiO_2$ [5], $HfO_2$ [8] and simple metal nitrides [10] or double metal oxide mixtures, such as TaAlO and ZrAlO [6] or combinations of two different amorphous metal oxide layers [11] and diamond like carbon (DLC) [9] that are relatively stable, apart from few exceptions [7], in a thermo dynamical manner in aqueous alkaline and oxidative environments. In particular, the introduction of metal oxides obtained significant improvements of pH sensor characteristics as well as long-term stability and drift of these sensors, in particular with respect to $Si_3N_4$-ISFETs.

Conventionally, metal oxides have been deposited and only tempered such that their amorphous structure is maintained. Thus, the same are chemically less stable and more light-sensitive than their crystalline counterparts in bulk chemistry and are subject to planar etching at increased temperature in corrosive media.

Crystalline simple metal oxide layers are chemically more stable than amorphous layers, since crystallites have a high density comparable to the bulk material. The weaknesses of these layers are the grain boundaries of the crystallites, in particular the vertical ones allowing pore etching and consequences of sub-etching at increased temperature in aggressive media. Thus, stable operation of sputtered and crystallized $Ta_2O_5$-ISFETs can only be ensured up to a pH value of approximately 12 and a temperature up to 75° C.

In multilayered polycrystalline metal oxides of one substance type, the vertical grain boundaries are only insufficiently interrupted since the crystals of the first layer act as growth seeds for the second layer.

Multilayered amorphous metal oxides of different substances are chemically more stable than simple ones, but the problems accompanying amorphous structures could not be satisfactorily solved.

The crystallizations of these multilayers of different metal oxide layers are, as can be expected, again chemically more stable, but the interfaces between the substance types result in typical interface problems. These are poor reproducibility of the flat band voltage and so-called charge trapping.

The deposition of metals with subsequent thermal oxidation [12] results, for kinetical reasons, in poor quality of the semiconductor/insulator combination, such as $Si/SiO_2$, since the metal has a reducing effect on an applied insulator (e.g., $SiO_2$) and thereby partly removes the oxygen from the insulator layer. This results in fixed charges in the gate insulator causing operating point shifts of the sensor and drifts by trapping processes. The trapping processes result in leakage currents which affect the chemical stability of the whole insulator stack.

Pure metal oxides have the features characteristic for its substance which can significantly differ from other metal oxides, such as $HfO_2$. Currently, $HfO_2$ is more frequently used due to its excellent chemical and physical characteristics as crystalline bulk material, both in sensor technology as well as in highly integrated microprocessor technology. Such features are the extremely high electric isolation values as well as the extremely high chemical resistance in aggressive media up to the commonly highest applied temperature. However, as a layer, it has a distinctive structure and mainly vertical grain boundaries [14].

The same responds to the temperings necessitated for stabilization and compression with extensive anisotropic thermal expansions which can lead to cracks in the layer at topology edges. Pure metal oxides mostly maintain their features characteristic for their substances even when stacked with others. Packing a thick $HfO_2$ layer between a base and a cover layer of a previously and subsequently deposited different metal oxide, such as $Ta_2O_5$, does not change the essential behavior of $HfO_2$. Even when $HfO_2$ is deposited in one or several thin amorphous layers and tempered with $Ta_2O_5$, the charges at the interfaces and in the $HfO_2$ layer itself are only difficult to control. Consequences are sensor drifts and light sensitivities that are not so small as they can be adjusted by $Ta_2O_5$ in a reproducible manner although the chemical stabilities are much greater [16].

Metal oxynitrides and also double metal oxynitride mixtures such as compounds such as, for example, $Hf_xTa_yO_aN_b$

[15] induce interfaces between the oxynitrid and the SiO$_2$ that are electrically hard to control.

SUMMARY

According to an embodiment, an ion-sensitive structure may have: a semiconductor structure; and a layer stack disposed on the semiconductor structure with a doped intermediate layer comprising a doping material and a first metal oxide material; wherein the semiconductor structure is configured to change an electric characteristic based on a contact of the ion-sensitive structure with an electrolyte comprising ions.

Another embodiment may have an electrolyte-insulator structure having an inventive ion-sensitive structure.

According to another embodiment, a method for producing an ion-sensitive structure may have the steps of: providing a semiconductor structure; and disposing a layer stack with a doped intermediate layer on the semiconductor structure; wherein disposing the layer stack comprises a step of producing the intermediate layer such that a first metal oxide material is doped with a doping material; such that the semiconductor structure is configured to change an electric characteristic based on a contact of the ion-sensitive structure with an electrolyte comprising ions.

The present invention is based on the knowledge that doping of a metal oxide intermediate layer can be used for obtaining a layer having high compactness and a low number of structural defects such that the layer also has high chemical resistance. This is obtained due to the fact that, based on the doping, a number of vertical grain boundaries in the layers and in layer transitions are reduced and/or an arrangement of different substances in different layers resulting in an abrupt change of the metal oxide structure is avoided.

The impurity atoms of the doping can be fixed in the lattice structure and can be locally bonded in the metal oxide, such that the same are not subject to any or merely low diffusion within the operating range. The impurity atoms can, for example, only be released by etching, such that extremely high chemical and thermal stability is obtained. Doping can be inexpensively integrated in an existing production process.

According to the present invention, an ion-sensitive structure includes a semiconductor structure and layer stack disposed on the semiconductor structure with a doped intermediate layer comprising a doping material and a metal oxide material. The semiconductor structure can comprise a semiconductor substrate and in particular a processed semiconductor substrate, wherein, in particular, semiconductor substrates or semiconductor structures are stated which are processed and implemented to change an electric characteristic based on a contact of the ion-sensitive structure with an electrolyte comprising ions. Thus, the semiconductor structure can be configured to change an electric conductivity, a capacitive characteristic or another electric characteristic based on the contact of the ion-sensitive structure with the electrolyte. Simply put, based on the changed electric characteristic, the contact of the ion-sensitive structure with the electrolyte or with the ions can be determined, such that the ion-sensitive structure is particularly suitable for arrangements in a suitable sensor. This includes electrolyte-insulator-sensor structures (EIS). Even in extremely aggressive media, the ion-sensitive structure has high chemical and electric resistance.

By means of the inventive ion-sensitive structure, an improved stability and sensitivity with regard to the ions to be detected is obtained with respect to previously used metal oxides, wherein further low cross-sensitivity and minimum drift is obtained at good long-term stability of a sensor comprising the ion-sensitive structure. This is, for example, obtained since doping of the metal oxide material results in a reduction of structural defects in the layer in comparison to a number of structural defects of the metal oxide material without presence of a dopant.

BRIEF DESCRIPTION OF THE DRAWINGS

Embodiments of the present invention will be detailed subsequently referring to the appended drawings, in which.

DETAILED DESCRIPTION OF THE INVENTION

Before embodiments of the present invention will be discussed in detail based on the drawings, it should be noted that identical, functionally equal or similar elements, object and/or structures are provided with the same reference numbers in the different figures, such that the description of these elements represented in different embodiments is inter-exchangeable or can be applied to one another.

Figure 1:
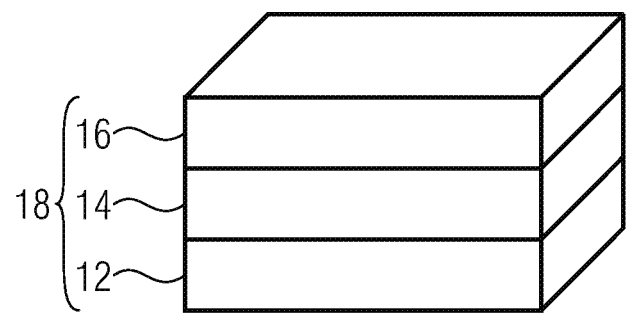
FIG. 1 is a schematic perspective view of an ion-sensitive structure according to an embodiment.

FIG. 1 shows a schematic perspective view of an ion-sensitive structure 10 according to an embodiment. The ion-sensitive structure 10 includes a semiconductor structure 12. The semiconductor structure 12 can, for example, be a processed semiconductor substrate. The processed semiconductor substrate can, for example, be a semiconductor substrate suitable for a transistor, which comprises npn or pnp structures.

A doped intermediate layer 14 is disposed on a main side of the semiconductor structure 12. The doped intermediate layer 14 includes a doping material and a metal oxide material, wherein the metal oxide material is formed, for example, of a metal material and oxygen. The metal oxide can, for example, be tantalum oxide ($Ta_2O_5$), niobium oxide ($Nb_2O_5$), hafnium oxide ($HfO_2$), another metal oxide or a mixture thereof. The doping material can be any material. Advantageously, such substances, e.g. metal materials having a lower number of outer electrons than the metal material of the intermediate layer 14 can be disposed. A compression of the doped intermediate layer can be obtained at least partly by the fact that a metal atom of the doping material having less outer electrons than the host lattice metal atom (metal material of the intermediate layer), e.g., Ta in $Ta_2O_5$ introduces accordingly less oxygen atoms in an oxidized state. Resulting gaps in the host lattice can be reduced, for example, by differences of the electronegativity between host atom and doping atom (e.g., Ta with 5 outer electrons and Ca with 2 outer electrons). This enables compression of the crystal lattice of the metal oxide material based on the doping material. The doping material can, for example, be calcium oxide material, strontium oxide material, magnesium oxide material, calcium silicate material, magnesium silicate material or strontium silicate material. Alternatively or additionally, the doping material can also be a mixture of materials. For example, a mixture including calcium oxide material and strontium oxide material, a mixture including calcium oxide material and magnesium oxide material and/or a mixture including strontium oxide material and magnesium oxide material can be disposed. In addition to the above-stated doping materials, further doping materials can be disposed. For a better understanding, the above-stated doping materials are referred to as first group of doping materials.

As will be discussed in connection with the below described embodiments, above this, further doping materials can be disposed in the intermediate layer 14. A second group of doping materials can include, for example, hafnium oxide material, zirconium oxide material, titanium oxide material, hafnium silicate material, zirconium silicate material or titanium silicate material. Alternatively or additionally, the first group can include a mixture of hafnium oxide material and zirconium oxide material, a mixture of zirconium oxide material and titanium oxide material, a mixture of hafnium oxide material and titanium oxide material, a mixture of hafnium oxide material and zirconium silicate material, a mixture of zirconium silicate material and titanium oxide material and/or a mixture of hafnium silicate material and titanium oxide material. A third group of doping materials includes the third sub-group of the periodic system, for example, scandium, ytrium and/or lanthanum and, alternatively or additionally, rare earth metals. The lanthanides or lanthanoides can be considered, for example, as rare earth metals (rare earths). Alternatively or additionally, a mixture of above stated mixtures and/or a mixture of an above-stated material and above-stated mixture can be disposed.

A proportion of the doping materials or doping materials in the intermediate layer can, for example, be greater than or equal to 0.03% (300 ppm) and less than or equal to 20%, greater than or equal to 1% and less than or equal to 15% or greater than or equal to 1.5% and less than or equal to 10%. The proportion of the doping material can relate to a volume fraction, advantageously, however, a mass fraction of the doping material in the doped intermediate layer 14. Simply put, when the doping atom concentration is too high, the host metal oxide lattice can be transformed into a different unsuitable less stable lattice.

A sensor layer 16 is disposed on a main side of the intermediate layer 14 facing away from the semiconductor structure 12. The intermediate layer 14 is disposed between the sensor layer 16 and the semiconductor structure 12. While the intermediate layer 14 is illustrated such that the same is connected directly to the semiconductor structure 12 and the sensor layer 16, further layers can be disposed between the doped intermediate layer 14 and the sensor layer 16 and/or between the doped intermediate layer 14 and the semiconductor structure 12. The sensor layer 16 can be implemented to be contacted with the electrolyte, for example when the ion-sensitive structure 10 is configured as ion-sensitive sensor for detecting or sensing the ions in the electrolyte. Contact of the sensor layer with the ions can result in a change of an electric characteristic of the semiconductor structure 12. Further, the sensor layer can also be considered as protective layer with respect to an underlying layer structure.

The sensor layer 16 can include a metal oxide material or consist of the same. The metal oxide material can be the tantalum oxide material, the niobium oxide material and/or the hafnium oxide material. The metal oxide material of the sensor layer 16 can differ from the metal oxide material of the intermediate layer 14. Alternatively, the two metal oxide materials can be the same. This allows a simple production process and a low measure of lattice vacancies between the layers when the molecules of the metal oxide materials essentially have the same size.

The intermediate layer 14 and the sensor layer 16 can also be considered as layer stack 18, wherein the layer stack 18 is disposed on the semiconductor structure 12.

The semiconductor structure 12 is configured to change an electric characteristic of the semiconductor structure 12 based on a contact of the ion-sensitive structure 10 with an electrolyte comprising ions. The electric characteristic can, for example, be a breakdown voltage, an electric resistance, an electric capacitance or the same which is disposed on or between structures of the semiconductor structure 12 or which is processed into the same. It can, for example, be an electric characteristic between a pn and/or an np junction. For example, if the sensor layer 16 is brought into contact with the electrolyte, the same can be sensed or measured on the semiconductor structure 12 based on the changed electric characteristic.

The ion-sensitive structure 10 can be configured as electrolyte-insulator structure (EIS structure). For this, an insulator layer can be disposed, for example, between the semiconductor structure 12 and the doped intermediate layer 14. The insulator layer can be part of the layer stack 18.

The above described doped intermediate layer 14 has a high compactness, in particular suitable for chemically aggressive environments. Compared to an intermediate layer that does not comprise the doping materials, a structure lattice of the layer can be compressed based on the doping materials. Due to the compactness of the lattice structure of the intermediate layer 14 or the metal oxide material based on the doping material, an extent of pore formation, in particular of the vertical pores is reduced. Here, the designation vertical pores relates to a shape of pores through the layer in a direction of adjacent layers and is not to be considered as limiting with regard to a spatial arrangement of the layers. The reduction of vertical pores allows the reduction or prevention of sub-etching of the doped intermediate layer 14 resulting in high stability and resistance of the layer structure. A further basis for high stability and resistance is the greater bonding strength between doping atom and metal oxide with respect to similar metal oxide molecules. This allows reliable operation of the ion-sensitive structure in a (chemically) aggressive environment.

In the following, based on FIG. 2a-f, a method for producing an ion-sensitive structure will be explained. The method relates to disposing the layer stack on the semiconductor structure. Disposing the layer stack will subsequently be discussed such that several layers are disposed on the semiconductor structure or another layer. The layers can be disposed by a sputter process, by a process for electron-beam evaporation, by a process including ion radiation, by chemical vapor deposition (CVD) and/or by physical vapor deposition (PVD). Producing or disposing individual layers can also include a process for thermal oxidation of a material and/or an ion implantation process. As the following explanations concerning the production method will show, the production of the inventive ion-sensitive structure or EIS layer structure for an ion-sensitive sensor can take place, for example, in a CMOS process.

Figure 2A:
FIG. 2a is a schematic provision of the semiconductor structure of a method for producing an ion-sensitive structure according to an embodiment.

FIG. 2a shows a provision of the semiconductor structure 12.

Figure 2B:
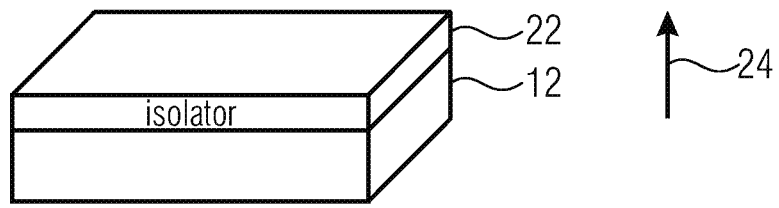
FIG. 2b is a schematic arrangement of an insulator layer on the semiconductor structure according to an embodiment.

FIG. 2b shows a disposal of an insulator layer 22 on the semiconductor structure 12. The insulator layer 22 can be disposed by thermal oxidation of a silicon material. The silicon material can be disposed on the semiconductor structure 12 prior to oxidation. Alternatively, the semiconductor structure 12 can already include the silicon material. If the semiconductor structure 12 includes, for example, silicon, silicon(di)oxide material ($SiO_2$) can be obtained based on the thermal oxidation. As stated in the context of FIG. 1, the layer stack disposed on the semiconductor structure 12 can comprise the insulator layer 22. Along a thickness direction 22 arranged parallel to a surface normal of the semiconductor structure 12 in space, the insulator layer 22 can have an expansion that is greater than or equal to 2 nm and less than or equal to 200 nm, greater than or equal to 2.5 nm and less than or equal to 150 nm or greater than or equal to 10 nm and less than or equal to 90 nm. Such a minimum expansion of the insulator layer can at least partly prevent that the doping material reaches the semiconductor structure 12 from the doped intermediate layer.

An expansion of one or several layers along the thickness direction 24 will subsequently be referred to as thickness of the respective layer, wherein the usage of the term "thickness" is not to be limiting in any sense. It is obvious that, based on any arbitrary spatial disposal of the structure, any other designations (such as length, height or width) can be used for designating the extension of the respective layer.

Figure 2C:
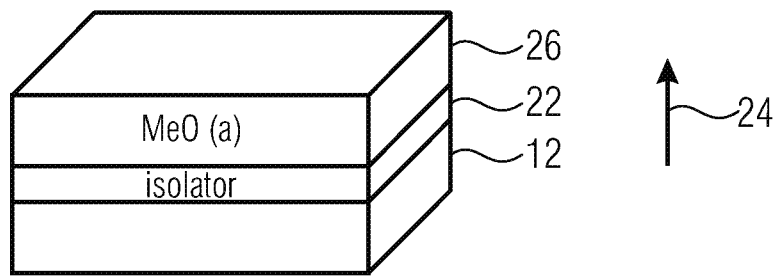
FIG. 2c is a schematic arrangement of a metal oxide layer on the insulator layer according to an embodiment.

FIG. 2c shows schematically a disposal of a metal oxide layer (metal Me; oxide O; MeO) 26 on the insulator layer 22. The metal oxide layer 26 can have an amorphous or polycrystalline structure as indicated by the designation (a). The metal oxide layer 26 has a layer thickness along the thickness direction 24, which is greater than or equal to 1 nm and less than or equal to 1000 nm, greater than or equal to 5 nm and less than or equal to 500 nm or greater than or equal to 12 nm and less than or equal to 200 nm. In the following, the metal oxide layer 26 is referred to as spacing layer, since one of the structural tasks of the metal oxide layer 26 can be the provision of a spacing between the further layer thickness and the insulator layer 22 or the semiconductor structure 12. In particular, the deposition of the spacing layer 26 can be performed such that the insulator layer 22 is chemically not influenced by the metal oxide deposition. Simply put, FIG. 2 shows a deposition of an amorphous metal oxide layer having a minimum layer thickness.

Figure 2D:
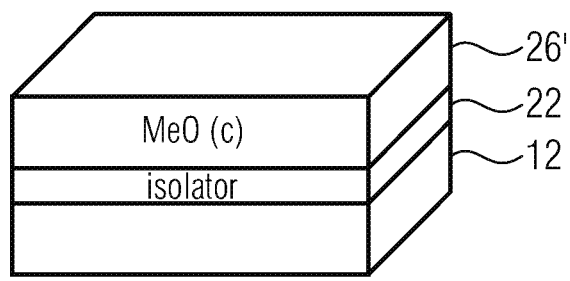
FIG. 2d is a schematic view of a layer structure after tempering of the layer structure described in FIG. 2c according to an embodiment.

FIG. 2d schematically shows the layer structure after tempering the layer structure described in FIG. 2c. Tempering can be performed such that crystallization of the metal oxide material of the spacing layer 26 takes place and such that based thereon a spacing layer 26' is obtained. The spacing layer 26' has at least partly a crystalline metal oxide material as indicated by the designation (c). The spacing layer 26' can be completely or partly formed of crystalline material. If the spacing layer 26' is partly formed of crystalline material (i.e., not completely crystallized during tempering), the spacing layer 26 can have a transition from the amorphous or polycrystalline structure towards the partly obtained (mono) crystalline structure. The amorphous or polycrystalline structure side of the spacing layer 26' is disposed, for example, facing the semiconductor structure 12. The crystalline structure side is disposed facing away from the semiconductor structure 12.

It is an advantage of the crystalline structure of the spacing layer 26' that diffusing of doping materials disposed subsequently on or in the spacing layer 26' is limited or prevented during tempering for fixing (annealing) the doping materials. Thus, a spacing of doped areas of the spacing layers forming a doped intermediate layer or another doped intermediate layer can have at least a minimum value discussed further below.

Figure 2E:
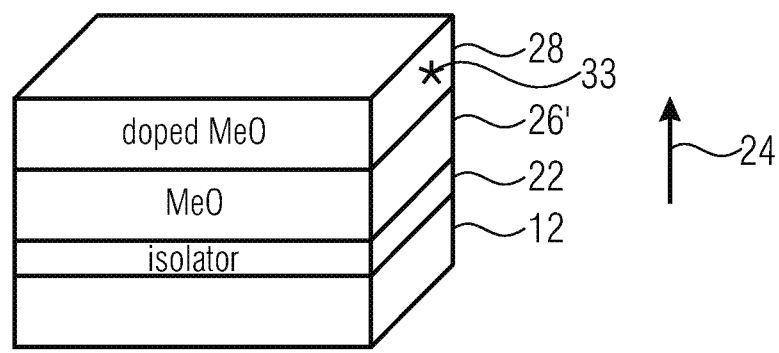
FIG. 2e is a schematic view of the layer stack of FIG. 2d after disposal of a doped intermediate layer on the tempered metal oxide layer according to an embodiment.

FIG. 2e shows schematically disposing or obtaining a doped intermediate layer 28 on the spacing layer 26. The doped intermediate layer 26 includes a metal oxide material and a doping material 33. As will be discussed below, the doped intermediate layer can be obtained, for example, by disposing and doping a metal oxide layer on the spacing layer 26. Alternatively, the doping material(s) can be disposed in the spacing layer 26, for example, by means of implantation. Implantation can be performed such that the doping material penetrates merely in a specific area or a specific depth opposite to the thickness direction 24 into the spacing layer 26. Based on an annealing of the spacing layer 26 comprising the implanted doping material(s), a doped intermediate layer 26 can be obtained from the spacing layer 26. A thickness (extension along the thickness direction 24) of the doped intermediate layer can, for example, be based on a penetration depth of the doping materials during implantation.

Figure 2F:
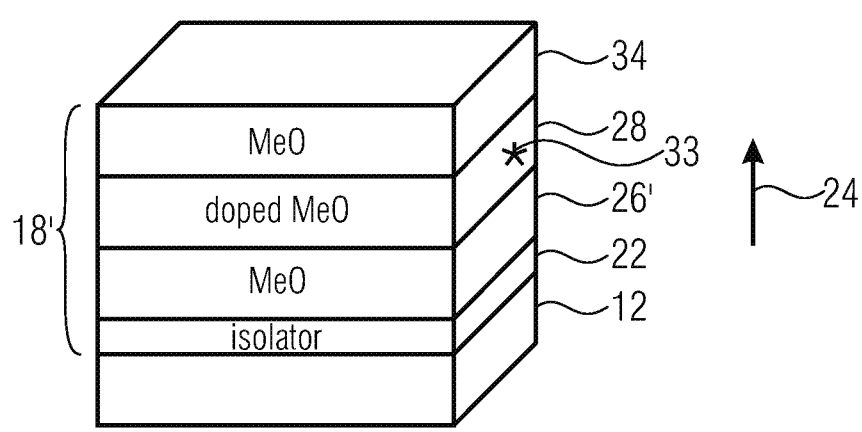
FIG. 2f is a schematic view of the layer stack of FIG. 2e after depositing a sensor layer according to an embodiment.

FIG. 2f shows depositing of a sensor layer 34 on the doped intermediate layer 28. The sensor layer 34 can comprise a metal oxide material which can be obtained based on depositing a metal oxide material or based on depositing and subsequent oxidation of a metal material. The sensor layer 34 can have a thickness along the thickness direction 24 of one angstrom (0.1 nm) or more and less than or equal to 150 nm. Alternatively, the sensor layer 34 can also have a layer thickness of less than or equal to 70 nm, advantageously less than or equal to 40 nm. The sensor layer 34 can, for example, be the sensor layer 16.

An ion-sensitive structure 20 including the semiconductor structure 12 and a layer stack 18' can be configured as electrolyte-insulator-structure. The electrolyte-insulator-structure can be configured as ion-sensitive field effect transistor, as ion-sensitive sensor or as light-addressable sensor (LAPS).

A (first) metal material of the intermediate layer 28 and a (second) metal material of the sensor layer 34 can be different from one another. Alternatively, the first metal material and the second metal material can be the same. This can have the effect that also the metal oxide materials are the same. A (third) metal material of the spacing layer 26' can be the same as the first and/or second metal material, such that the spacing layer 26' can have the same metal oxide material as the intermediate layer 28 and/or the sensor layer 34. In other words, the above-described embodiments allow that, based on the same metal oxide materials and/or a doping of a chemically relatively stable layer, such as $Ta_2O_5$, a sudden change of the metal oxide structure can be prevented as it is obtained when different substances, such as $Ta_2O_5$ and $HfO_2$, are disposed.

In the following, based on FIGS. 3a-f, an embodiment will be described by which the doped intermediate layer 14 or 28 can be obtained.

Figure 3A:
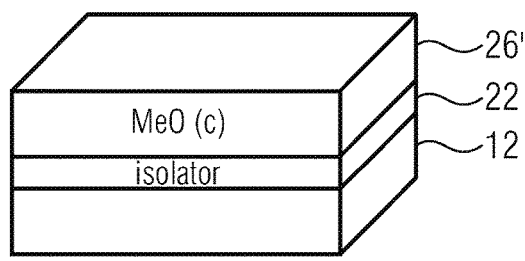
FIG. 3a is a schematic view of the layer stack of FIG. 2d.

FIG. 3a shows schematically a layer stack including the semiconductor structure 12, the insulator layer 22 and the spacing layer 26' as described in the context of FIG. 2d.

Figure 3B:
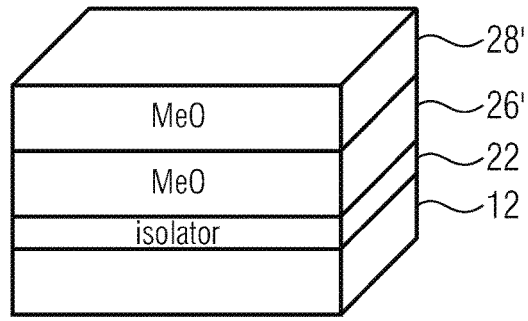
FIG. 3b a schematic view of a disposal of a metal oxide material on the spacing layer according to an embodiment.

FIG. 3b shows schematically a disposal of a metal oxide material on the spacing layer 26' such that a metal oxide layer 28' is obtained. The metal of the metal oxide layer 28' can be a metal or semimetal, for example tantalum, hafnium or niobium.

In other words, after tempering illustrated in FIG. 2d, wherein crystallization of the metal oxide (such as $Ta_2O_5$) can take place, a metal oxide material, such as tantalum oxide, is deposited in FIG. 2e.

Figure 3C:
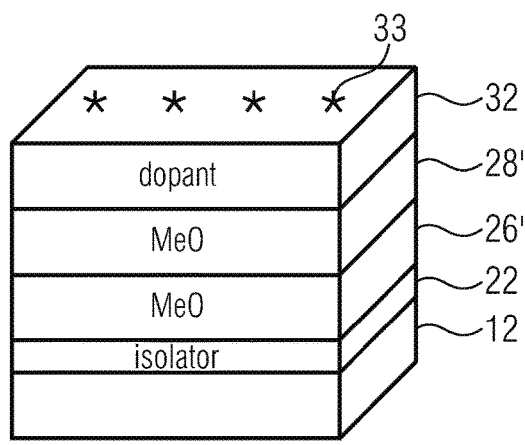
FIG. 3c is a schematic view of an arrangement of a layer with a doping material on the metal oxide material according to an embodiment.

FIG. 3c shows schematically the disposal of a layer 32 (donor layer) on the metal oxide layer 28. The layer 32 includes the at least one doping material 33. The same can be one or several of the groups of doping materials discussed in the context of FIG. 1.

Figure 3D:
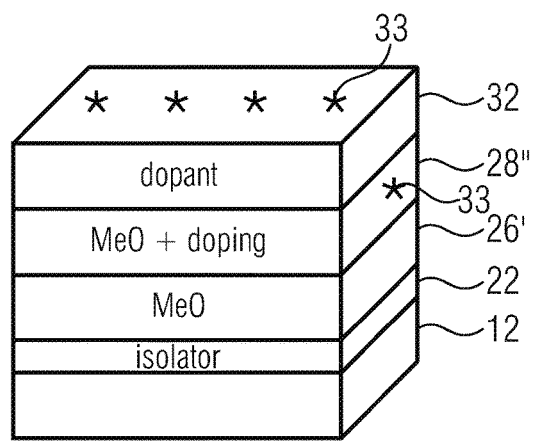
FIG. 3d is a schematic view of a crossing of the doping material into the metal oxide material according to an embodiment.

FIG. 3d shows schematically a crossing of the doping material 33 into the metal oxide layer 28', such that a modified metal oxide layer 28" can be obtained which includes the doping material 33. This can be performed, for example, by means of heating (tempering) which allows diffusing the doping material 33 into the metal oxide layer 28'. An amount of the doping material 33 and/or a curve of a doping profile described in the context of FIG. 6a-c can be influenced or controlled based on a temperature curve of the tempering.

Figure 3E:
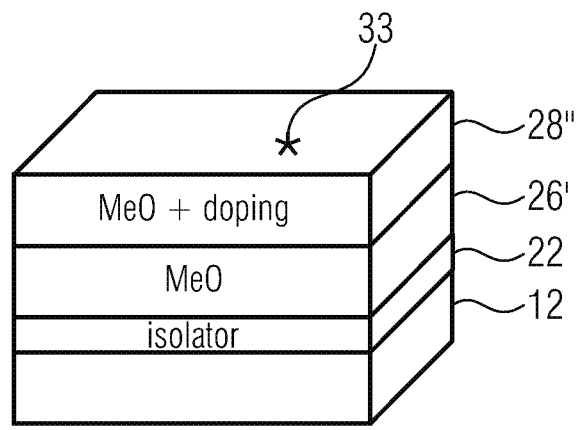
FIG. 3e is a schematic view of a removal of the layer with the doping material subsequent to tempering according to an embodiment.

FIG. 3e shows schematically a removal of the layer 32 from the layer stack following the tempering described in the context of FIG. 3d.

Figure 3F:
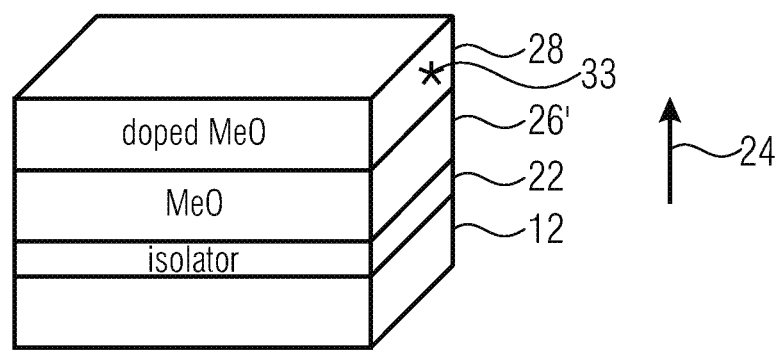
FIG. 3f is a schematic view of the layer stack after further tempering after the doping is annealed such that a doped metal oxide layer is obtained, according to an embodiment.

FIG. 3f shows schematically the layer stack after further tempering after which the doping of the layer 28" of FIG. 3e is annealed, such that the doped metal oxide layer 28 is obtained in which the doping material 33 is at least partly fixed. Fixing can be effected by bonding the doping material 33 into the crystal lattice of the metal oxide material. Based on the tempering, for example, re-crystallization of the metal oxide material by bonding (fixing) the doping material 33 can take place. The spacing layer 26' is disposed between the semiconductor structure 12 and the doped intermediate layer 28.

The steps illustrated in FIGS. 3c to 3f can be performed repetitively, for example for diffusing several dopants into the metal oxide layer 28'. The additional dopants described in the context of FIG. 1 of group 2 and/or group 3 can be disposed, for example, prior to disposing the dopants of group 1. Simply put, disposing the doping materials of group 2 and/or group 3 can take place prior to or after disposing the doping materials of group 1.

In the following, an alternative embodiment will be described based on FIGS. 4a-c by which the doped intermediate layer 14 or 28 can be obtained.

Figure 4A:
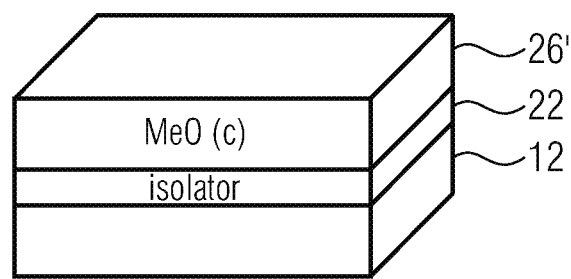
FIG. 4a is a schematic view of the layer stack of FIG. 2d.

FIG. 4a shows schematically the layer stack including the semiconductor structure 12, the insulator layer 22 and the spacing layer 26' as described in the context of FIG. 2d.

Figure 4B:
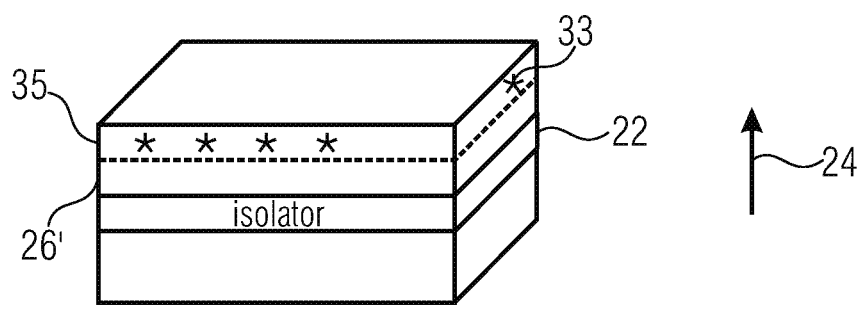
FIG. 4b is a schematic view of an arrangement of the doping material into the spacing layer by means of an implantation process according to an embodiment.

FIG. 4b shows schematically a disposal of the doping material 33 into the spacing layer 26' by means of an implantation process. By means of the implantation process, for example metal materials, of the respective doping material 33 are disposed in the spacing layer 26'. The metal material can, for example, be hafnium, zirconium, tantalum, calcium, magnesium, strontium and/or ions thereof. The implantation can be performed such that the metal materials merely penetrate into a depth region 35 opposite to the thickness direction 24 maintaining a minimum spacing of the spacing layer 26' in which only a few or none of the doping materials are disposed.

Figure 4C:
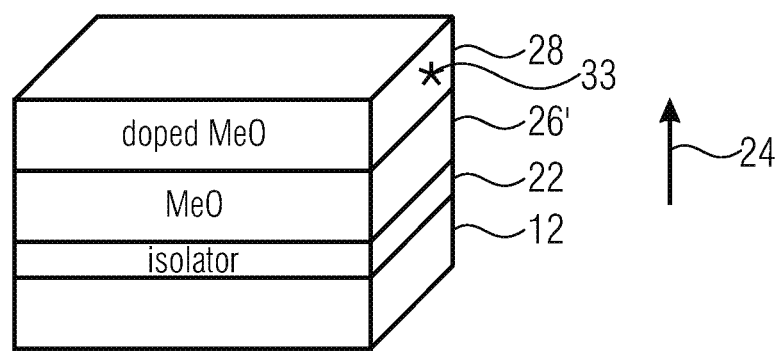
FIG. 4c is a schematic view of obtaining the doped intermediate layer based on the implanted metal materials according to an embodiment.

FIG. 4c shows schematically obtaining the doped intermediate layer 28 based on the implanted metal materials. The doped intermediate layer can be obtained by supplying oxygen and possibly by tempering the spacing layer 26' described in FIG. 4b. Tempering with oxygen supply allows for oxidation and annealing, such that the material recrystallizes in the area. Metal materials can oxidize such that recrystallization of the doped metal oxide material is obtained. Thereby, an intermediate layer 28 formed integrally with the spacing layer 26' can be obtained.

In the following, an alternative embodiment will be described based on FIGS. 5a-f by which the doped intermediate layer 14 or 28 can be obtained.

Figure 5A:
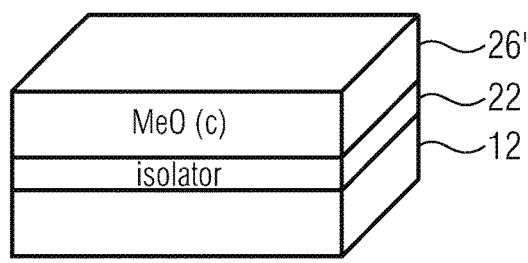
FIG. 5a is a schematic view of the layer stack of FIG. 2d.

FIG. 5a shows schematically the layer stack including the semiconductor structure 12, the insulator layer 22 and the spacing layer 26' as described in the context of FIG. 2d.

Figure 5B:
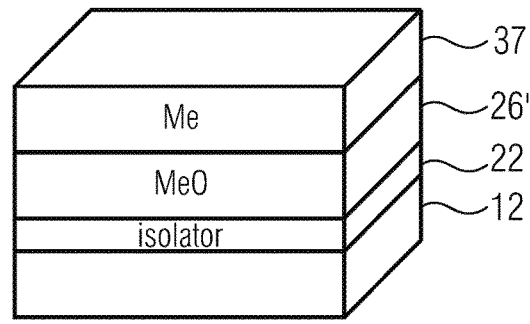
FIG. 5b is a schematic view of a disposal of the layer with a metal material on the spacing layer according to an embodiment.

FIG. 5b shows schematically a disposal of a layer 37 on the spacing layer 26'. The layer 37 includes the metal material of the doped intermediate layer 28, wherein the metal material can be in an unoxidized state.

Figure 5C:
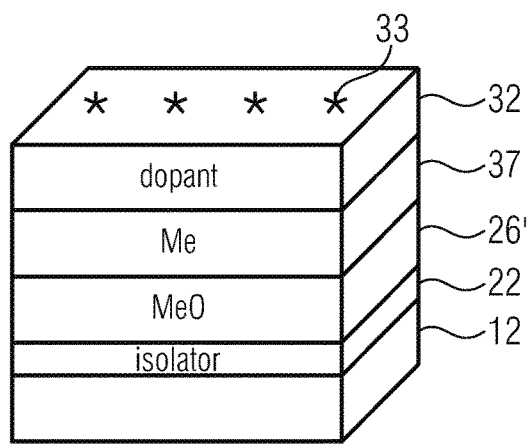
FIG. 5c is a schematic view of a disposal of the layer including the doping material on the layer including the metal material according to an embodiment.

FIG. 5c shows schematically a disposal of the layer 32 including the doping material 33 on the layer 37. Simply put, the layer 32 can be disposed on the layer 37 instead of on the layer 28' as described in the context of FIG. 3c.

Figure 5D:
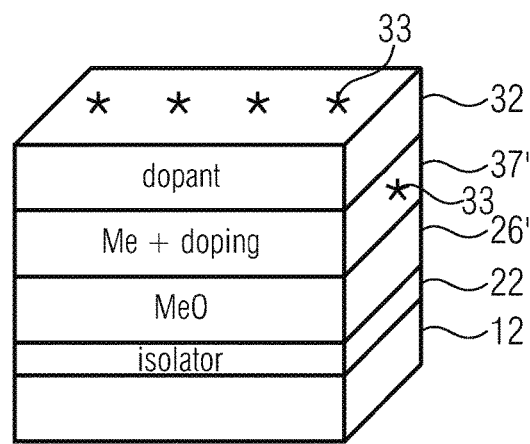
FIG. 5d is a schematic view of a crossing of the doping material into the layer including the metal material according to an embodiment.

FIG. 5d shows schematically a crossing of the doping material 33 into the layer 37 as described in the context of FIG. 3d. Based on the crossing of the doping material 33 into the layer 37, layer 37' can be obtained comprising the metal material and the doping material 33.

Figure 5E:
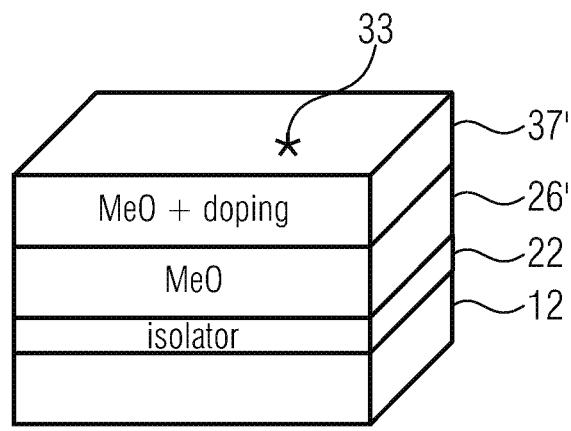
FIG. 5e is a schematic view of a removal of the layer including the doping material according to an embodiment.

FIG. 5e shows schematically the removal of layer 32 as described in the context of FIG. 3e.

Figure 5F:
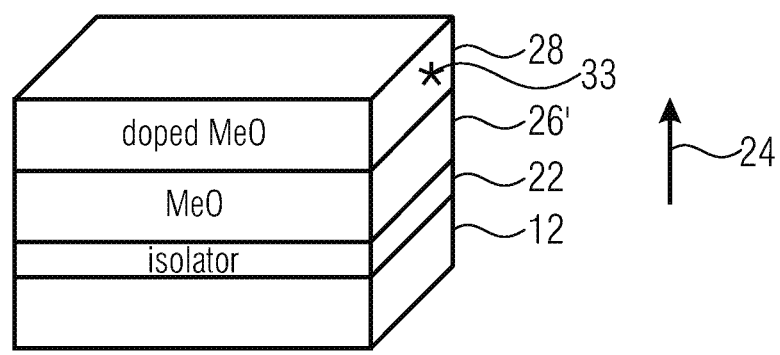
FIG. 5f is a schematic view of an oxidation of the metal material of the layer with the doping material and the metal material according to an embodiment.

FIG. 5f shows schematically oxidation of the metal material of the layer 37' and the doping material. This can be performed, for example, by supplying temperature and/or oxygen, such that simultaneous oxidation of the metal material and the doping material is obtained in the doped intermediate layer 28. Simply put, the doped intermediate layer 28 can also be obtained by performing the deposition of the metal oxide layer 28' described in the context of FIG. 3b such that the deposited material already at least partly comprises one doping material or several doping materials.

The layer 28 can, for example, be the intermediate layer 14. The intermediate layer 28 and/or the intermediate layer 14 can have a layer thickness along the thickness direction 24 of at least 1 nm and at the most 200 nm (for example of at least 1 nm and at the most 50 nm), of at least 3 nm and at the most 150 nm or at least 5 nm and at the most 100 nm.

Alternatively, the doped intermediate layer 28 can also be obtained by disposing a doped metal material layer on the spacing layer 26'. Thereupon, the doped metal material layer can be oxidized, for example thermally, such that the doped metal oxide material layer (intermediate layer) 28 is obtained.

The spacing layer 26' can reduce or prevent penetration of the doping material or the doping materials into the insulator layer 22 during the above-described production process. If the doped intermediate layer 28 is obtained by means of implantation of metals into the spacing layer 26', an implantation depth not exceeding the thickness of the spacing layer 26' is advantageous, such that the metal materials are kept at a distance (spaced apart) by the insulator layer 22.

Thus, a layer stack 18' can include the insulator layer 22, the spacing layer 26', the doped intermediate layer 28 and the sensor layer 34. Alternatively, as described above, the layer stack 18' can be configured such that the doped intermediate layer 28 is integrally formed with the spacing layer 26'.

Obtaining the doped intermediate layer can also be performed based on a combination of steps described in FIGS. 3a-f, FIGS. 4a-c and/or FIGS. 5a-f.

Figure 6C:
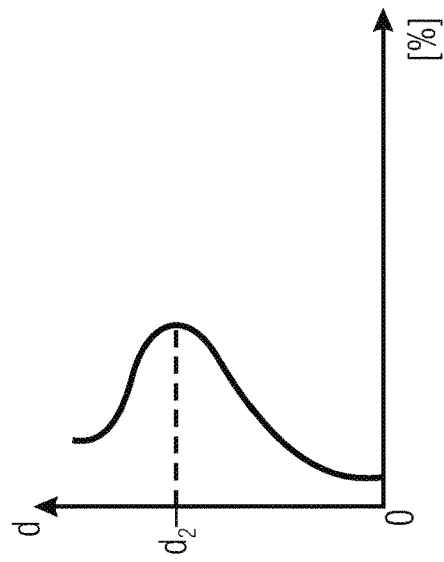
FIG. 6c is a schematic diagram with a non-monotonous curve of the concentration of the doping material along the thickness according to an embodiment.
Figure 6B:
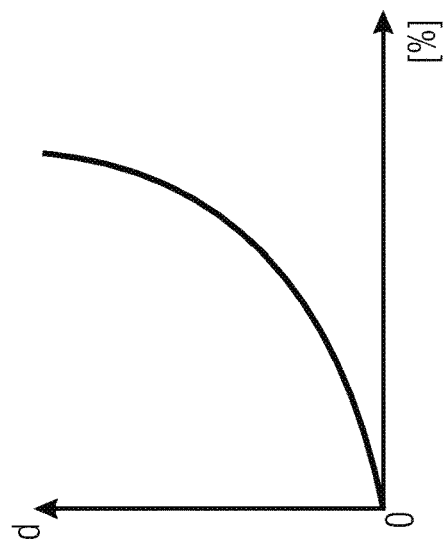
FIG. 6b is a schematic diagram with a non-linear curve of the concentration of the doping material along the thickness according to an embodiment.
Figure 6A:
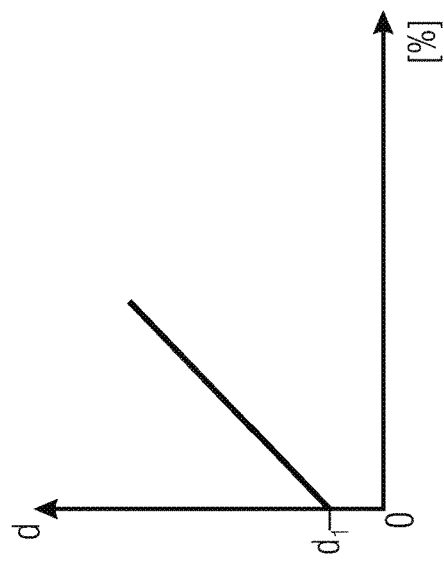
FIG. 6a is a schematic diagram with a linear increase of the concentration of the doping material along the thickness of the doped intermediate layer according to an embodiment.

FIGS. 6a-c show schematic diagrams with curves of a concentration of the doping material or its proportion in the doped intermediate layer 28 or 14 along a thickness d which can run along the thickness direction 24 of FIGS. 2a-f. The thickness d is plotted on the ordinate of the diagrams. A percentage of the doping material in the doped intermediate layer is plotted on the abscissa of the graphs.

FIG. 6a shows a schematic linear increase of the concentration of the doping material along the thickness d in the doped intermediate layer. If the doped intermediate layer is formed integrally with the spacing layer, the curve of the concentration can also relate to the spacing layer. In a thickness range starting from 0 up to a thickness $d_1$, the content of the doping material is, for example, 0 or approximately 0. The concentration of the doping material starts to rise with increasing thickness of the thickness $d_1$. This means that, for example, adjacent to the spacing layer 26' of FIG. 2f, no doping material or merely a small proportion can be contained. Alternatively, already at a thickness d=0, a proportion of the doping material of more than 0 can be contained, which can provide evidence that during the production of the doped intermediate layer a proportion of the doping material is diffused into the spacing layer.

FIG. 6b shows a schematic non-linear curve of the concentration of the proportion of the doping material along the thickness d. At a thickness d=0, a proportion of the doping material is, for example, also 0. Simply put, a proportion (concentration) of the doping material in the intermediate layer can decrease starting from the side of the intermediate layer facing away from the semiconductor structure in a direction towards the semiconductor structure.

FIG. 6c shows a schematic diagram with a non-monotonous curve of the concentration of the proportion of the doping material along the thickness d. Starting from a thickness d=0 (for example adjacent to the spacing layer), the proportion of doping material increases and has a maximum at a thickness $d_2$ and decreases again with increasing thickness d.

Basically, any curves of the concentration of the doping material in the doped intermediate layer can be obtained. By sequentially arranging different doping materials or layers comprising the doping material and/or different tempering, diffusing the doping material into the metal oxide material and through the same can be influenced. When sequentially providing doping materials and/or based on different molecule sizes of the doping material, diffusion of individual doping materials can also be influenced.

A field of application of the above described ion-sensitive structures is, for example, pH measurement technology. Above described embodiments allow fast checking of surface state in situ.

By doping and tempering, a doping profile with increasing and/or decreasing concentration of the dopant (doping material) can be adjusted. Improved structural adjustment and prevention of structural defects in the layer (intermediate layer) can result. By doping with strongly polarizing metal atoms that are merely movable at high temperatures, such as calcium (Ca), a metal oxide structure can be produced in a structurally more compressed manner and with Lewis amphoteric metal oxides, such as $HfO_2$, strong polarization of the lattice can be relaxed again. After layer production, tempering can adjust the doping concentration and the doping profile.

The above described embodiments further allow that the substance does not have to be left. This means the actual host lattice of the metal oxide (e.g., Ta2O5) can be deposited and tempered, such that at the same temperature the same lattice structure of the same crystal type can be obtained. The same can remain unamended as long as the dopant concentration does not exceed a critical amount. Thereby, possibly serious structural disorders can be prevented. For sensory applications of the respective apparatus, high or even highest insensitivity to foreign ions can be obtained or maintained. Impurity atoms fixed once (doping materials), such as calcium, are locally bound and are not subject to any further diffusion during operation as long as the operating conditions do not exceed respective temperatures such as, for example, 150° C. In such a case, the introduced impurity atoms can only be released by etching. For example, calcium tantalates (doped intermediate layer including tantalum oxide and calcium doping materials) as well as derivatives are chemically and thermally extremely stable as described, for example, in [17] and [18].

In other words, if the layer thickness of the insulator layer 22 falls below a minimum layer thickness, subsequently disposed doping material can diffuse into the interface layer of the amorphous insulator material ($SiO_2$) to the semiconductor substrate (Si), when applying high temperature during annealing, and possibly unintentionally shift the flatband voltage of an EIS structure as well as the insulation behavior.

After depositing the doping material, this layer can be removed after further tempering where this dopant is diffused into the metal oxide ($Ta_2O_5$) and further tempering can be performed to anneal and fix the doping. Subsequently, a further layer including metal oxide can be deposited or a further metal can be deposited and thermally oxidized. Further tempering can change the doping profiles again. Advantageously, the last layer (sensor layer) does not fall below a specific thickness. The thickness can depend on the metal oxide, according to the above doping profile (doping profile of the doped intermediate layer adjacent to the sensor layer), such that no unnecessitated amount of dopant reaches the protective layer surface and a sensor sensibility and impurity ion sensibility, when used, is amended in an unfavorable manner.

By the inventive procedure for producing an ion-sensitive layer structure for an ion-sensitive sensor, such as an ISFET, a capacitively readable EIS sensor or an LAPS sensor, in particular the lifespan in chemically aggressive media, such as during a CIP process (CIP=cleaning in place) can be significantly increased, even at relatively high temperatures. Thus, in a respectively formed ion-sensitive sensor, such as an ISFET, the operating point drift or also the flatband voltage can be significantly reduced compared to conventionally configured ion-sensitive sensors at thermal sterilization conditions with hot water vapor, such as an SIP process (SIP=sterilization in place), for example at temperatures of up to 135° C.

While some aspects have been described in the context of an apparatus, it is obvious that these aspects also represent a description of the respective method, such that a block or device of an apparatus can also be considered as a respective method step or as a feature of a method step. Analogously, aspects that have been described in the context of one or as a method step also represent a description of a respective block or detail or feature of a respective apparatus.

While this invention has been described in terms of several advantageous embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations, and equivalents as fall within the true spirit and scope of the present invention.

LITERATURE

[1] Bergveld, Development of an ion-sensitive solid-state device for neurophysiological measurements, IEEE Trans. Biomed. Eng. BME-17 (1970), p. 70.

[2] "Chemical Sensitivity of an ISFET with $Ta_2O_5$ membrane in strong acid and alkaline solutions", P. V. Bobrov, et al., Leningrad State University USSR, Sensors and Actuators B 3 (1991) 75-81.

[3] "The pH-sensing properties of tantalum pentoxide films fabricated by metal organic low pressure chemical vapor deposition", T. Mikolajick, et al., Fraunhofer Institute integrated Circuits Erlangen Germany, Sensors and Actuators B 44 (1997) 262-267.

[4] Sensitivity and hysteresis effect in $Al_2O_3$ gate phISFET, Jung-Chuan Chou et al., National Yunlin University Taiwan, Materials Chemistry and Physics 71 (2001) 120-4.

[5] "Study of $TiO_2$ thin films for Ion-sensitive Field Effect Transistor Application with RF sputtering deposition", Jung Chuan Chou, Lan Pin Liao, National Yunlin University of Science & Technology, Taiwan, Japanese Journal of Applied Physics 43, 1, 2004 p. 61-65.

[6] "Development of a wide range pH sensor based on Elektrolyt-Insulator-Semiconductor structure with corrosion-resistant $Al_2O_3$—$Ta_2O_5$ and $Al_2O_3$—$ZrO_2$ double-oxide thin films", Shoji Yoshida, et al., Tohoku University Sendai Japan, J. Electrochem. Soc. 151 (3) H53-H58 (2004).

[7] "pH sensitivity improvement on 8 nm thick Hafnium oxide by post deposition annelaing", Chao-Sung Lai et al., Chang Gung University Tao-Yuan Taiwan, Electrochemical and Solid-State Letters 9 (3) G90-2 (2006).

[8] P. D. van der Wal et al., Proceedings of IEEE Sensors (2004) 677.

[9] H. Voigt et al., Sensors & Actuators 44 (1997) 1-3, 441.

[10] U.S. Pat. No. 5,288,563

[11] International patent WO2005/073706

[12] P. Gimmel et al., Sensors & Actuators 4 (1991) 1-2, 135

[13] Hafeman et al., Science 240 (1988) 1182

[14] H. Grüger et al., Thin Film Solids 447-448 (2004) 509

[15] U.S. Pat. No. 7,321,143

[16] U.S. Pat. No. 8,461,587 B2 Multilayer

[17] H. Remy, Lehrbuch der anorganischen Chemie, volume II, 12th edition, Leipzig 1973, Akad. Verlagsges. Geest & Portig/18/R. C. Roop, Encyclopedia of the alkaline earth compounds, Elsevier 2013, p. 772.

The invention claimed is:

1. Ion-sensitive structure comprising:
    a semiconductor structure; and
    a layer stack disposed on the semiconductor structure, the layer stack having a doped intermediate layer comprising a doping material and comprising a first metal oxide material;
    wherein the semiconductor structure is configured to change an electric characteristic based on a contact of the ion-sensitive structure with a liquid electrolyte comprising ions; and
    wherein the intermediate layer comprises a mass fraction of the doping material which is greater than or equal to 0.03% and less than or equal to 20% with regard to a mass fraction of the metal oxide material.

2. Ion-sensitive structure according to claim 1, wherein the layer stack comprises an insulator layer disposed between the semiconductor structure and the intermediate layer.

3. Ion-sensitive structure according to claim 2, wherein the insulator layer comprises a layer thickness along a direction parallel to a surface normal of the semiconductor of at least 2 nm and at the most 200 nm.

4. Ion-sensitive structure according to claim 1, wherein the layer stack comprises a sensor layer comprising a second metal oxide material, wherein the intermediate layer is disposed between the semiconductor structure and the sensor layer, and wherein the sensor layer is configured to be contacted with the electrolyte and wherein the ion-sensitive structure is configured as ion-sensitive sensor.

5. Ion-sensitive structure according to claim 4, wherein the sensor layer comprises a layer thickness along a direction parallel to a surface normal of the semiconductor structure of at least 0.1 nm and at the most 150 nm.

6. Ion-sensitive structure according to claim 4, wherein the first metal oxide material and the second metal oxide material is the same.

7. Ion-sensitive structure according to claim 1, wherein the layer stack comprises a spacing layer that is disposed between the semiconductor structure and the intermediate layer and that comprises a third metal oxide material.

8. Ion-sensitive structure according to claim 7, wherein the spacing layer comprises a layer thickness along a direction parallel to a surface normal of the semiconductor structure of at least 5 nm and at the most 1000 nm.

9. Ion-sensitive structure according to claim 1, wherein the first metal oxide material comprises tantalum oxide and/or niobium oxide.

10. Ion-sensitive structure according to claim 1, wherein a proportion of the doping material in the intermediate layer decreases starting from a side of the intermediate layer facing away from the semiconductor structure in a direction towards the semiconductor structure.

11. Ion-sensitive structure according to claim 10, wherein the concentration of the doping material is zero at the side directed towards the semiconductor structure.

12. Ion-sensitive structure according to claim 1, wherein the doping material is one of calcium oxide, strontium oxide, magnesium oxide, calcium silicate, magnesium silicate, strontium silicate, a mixture comprising calcium oxide and strontium oxide, a mixture comprising calcium oxide and magnesium oxide and a mixture comprising strontium oxide and magnesium oxide.

13. Ion-sensitive structure according to claim 12, wherein the intermediate layer comprises a first further doping material which is one of hafnium oxide, zirconium oxide, titanium oxide, hafnium silicate, zirconium silicate, titanium silicate, a mixture comprising hafnium oxide and zirconium oxide, a mixture comprising zirconium oxide and titanium oxide, a mixture comprising hafnium oxide and titanium oxide, a mixture comprising hafnium oxide, zirconium silicate, a mixture comprising zirconium silicate and titanium oxide, and a mixture comprising hafnium silicate and titanium oxide.

14. Ion-sensitive structure according to claim 12, wherein the intermediate layer comprises a second further doping material comprising one of a group of substances comprising the third group of the periodic system and rare earth metals.

15. Ion-sensitive structure according to claim 1, wherein the intermediate layer comprises a layer thickness of at least 1 nm and at the most 200 nm.

16. Ion-sensitive structure according to claim 1, wherein the intermediate layer comprises a junction from an amorphous or polycrystalline structure side towards a crystalline structure side, wherein the amorphous or polycrystalline structure side is facing the semiconductor structure and the crystalline structure side is facing away from the semiconductor structure.

17. Ion-sensitive structure according to claim 1, wherein the electric characteristic is implemented at or between structures of the semiconductor structure, or is processed into the structures of the semiconductor substrate.

18. Electrolyte-insulator structure comprising an ion-sensitive structure according to claim 1.

19. Ion-sensitive structure according to claim 18, which is configured as ion-sensitive field effect transistor, as ion-sensitive sensor or as light-addressed sensor.

20. Ion-sensitive structure according to claim 1, wherein the intermediate layer comprises a mass fraction of the doping material which is greater than or equal to 0.1% and less than or equal to 15% with regard to a mass fraction of the metal oxide material.

21. Ion-sensitive structure comprising:
a semiconductor structure; and
a layer stack disposed on the semiconductor structure, the layer stack having a doped intermediate layer comprising a doping material and comprising a first metal oxide material;
wherein the semiconductor structure is configured to change an electric characteristic based on a contact of the ion-sensitive structure with an electrolyte comprising ions;
wherein the intermediate layer comprises a mass fraction of the doping material which is greater than or equal to 0.03% and less than or equal to 20% with regard to a mass fraction of the metal oxide material; and
wherein the layer stack comprises a sensor layer comprising a second metal oxide material, wherein the intermediate layer is disposed between the semiconductor structure and the sensor layer, and wherein the sensor layer is configured to be contacted with the electrolyte and wherein the ion-sensitive structure is configured as ion-sensitive sensor.

22. Ion-sensitive structure comprising:
a semiconductor structure; and
a layer stack disposed on the semiconductor structure, the layer stack having a doped intermediate layer comprising a doping material and comprising a first metal oxide material;
wherein the semiconductor structure is configured to change an electric characteristic based on a contact of the ion-sensitive structure with an electrolyte comprising ions;
wherein the layer stack comprises a sensor layer comprising a second metal oxide material, wherein the intermediate layer is disposed between the semiconductor structure and the sensor layer, and wherein the sensor layer is configured to be contacted with the electrolyte and wherein the ion-sensitive structure is configured as ion-sensitive sensor;
wherein the layer stack comprises a spacing layer that is disposed between the semiconductor structure and the intermediate layer and that comprises a third metal oxide material; and
wherein the intermediate layer comprises a mass fraction of the doping material which is greater than or equal to 0.03% and less than or equal to 20% with regard to a mass fraction of the metal oxide material.

23. Ion-sensitive structure comprising:
a semiconductor structure; and
a layer stack disposed on the semiconductor structure, the layer stack having a doped intermediate layer comprising a doping material and comprising a first metal oxide material;
wherein the semiconductor structure is configured to change an electric characteristic based on a contact of the ion-sensitive structure with a liquid electrolyte comprising ions and is configured for pH measurements;
wherein the layer stack comprises a sensor layer comprising a second metal oxide material, wherein the intermediate layer is disposed between the semiconductor structure and the sensor layer, and wherein the sensor layer is configured to be contacted with the electrolyte and wherein the ion-sensitive structure is configured as ion-sensitive sensor;
wherein the layer stack comprises a spacing layer that is disposed between the semiconductor structure and the intermediate layer and that comprises a third metal oxide material;

wherein a proportion of the doping material in the intermediate layer decreases starting from a side of the intermediate layer facing away from the semiconductor structure in a direction towards the semiconductor structure;
wherein the intermediate layer comprises a mass fraction of the doping material which is greater than or equal to 0.03% and less than or equal to 20% with regard to a mass fraction of the metal oxide material.

* * * * *